US00PP30066P2

(12) United States Plant Patent
Verhoef

(10) Patent No.: US PP30,066 P2
(45) Date of Patent: Jan. 8, 2019

(54) ***WEIGELA* PLANT NAMED 'TVP2'**

(50) Latin Name: *Weigela florida*
Varietal Denomination: TVP2

(71) Applicant: Gijsbertus Verhoef, Hazerswoude-Dorp (NL)

(72) Inventor: Gijsbertus Verhoef, Hazerswoude-Dorp (NL)

( * ) Notice: Subject to any disclaimer, the term of this patent is extended or adjusted under 35 U.S.C. 154(b) by 0 days.

(21) Appl. No.: 15/732,356

(22) Filed: Oct. 30, 2017

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Penny J. Aguirre

(57) ABSTRACT

A new cultivar of *Weigela florida*, 'TVP2', characterized by its a very compact plant habit, its freely-branching habit, its foliage that is vibrant green in color, its fine foliage, its floriferous, remontant blooming habit and its flowers that are deep pink in color.

2 Drawing Sheets

Botanical classification: *Weigela florida.*
Variety denomination: 'TVP2'.

BACKGROUND OF THE INVENTION

The present invention relates to a new and distinct cultivar of *Weigela* and will be referred to hereafter by its cultivar name, 'TVP2'. 'TVP2' represents a new cultivar of *Weigela*, a deciduous shrub grown for landscape use.

The new cultivar originated as a seedling in a trial field that was planted with seeds collected numerous open pollinated named and unnamed *Weigela* plants in Hazerswoude-Dorp, The Netherlands. 'TVP2' was selected as a single unique plant in July of 2016.

Asexual propagation of the new cultivar was first accomplished by softwood stem cuttings by the Inventor in July of 2016 in Hazerswoude-Dorp, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'TVP2' as a unique cultivar of *Weigela.*

1. 'TVP2' exhibits a very compact plant habit.
2. 'TVP2' exhibits a freely branching habit.
3. 'TVP2' exhibits foliage that is vibrant green in color.
4. 'TVP2' exhibits fine foliage.
5. 'TVP2' exhibits floriferous, remontant blooming habit.
6. 'TVP2' exhibits flowers that are deep pink in color.

'TVP2' can be compared to the *Weigela florida* varieties 'Plangen' (not patented) 'Slingpink' (U.S. Plant Pat. No. 29,149). Both 'Plangen' and 'Slingpink' are similar to 'TVP2' in having foliage that is green in color and flowers that are pink in color. 'Plangen' differs from 'TVP2' in having a less compact plant habit, flowers that are lighter pink in color, foliage that is less fine and in being less freely branched. 'Slingpink' differs from 'TVP2' in having a less compact plant habit, flowers that are white and light pink in color, foliage that is less fine, and in being less freely branched.

BRIEF DESCRIPTION OF THE DRAWINGS

The accompanying colored photographs were taken in August and illustrates the overall appearance and distinct characteristics of 14 month-old plants the new *Weigela* as grown outdoors in a field Hazerswoude-Dorp, The Netherlands.

The photograph in FIG. 1 provides an overall view of the growth habit of 'TVP2'.

Figure 1:
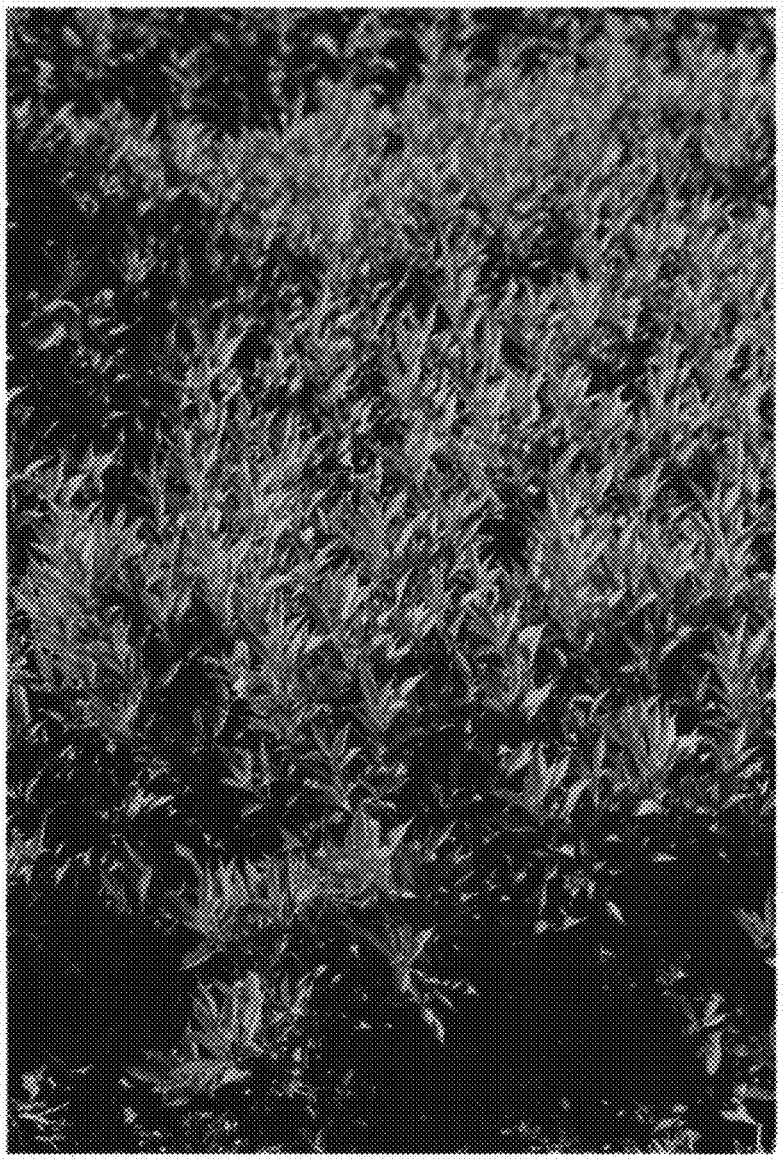
Figure 2:
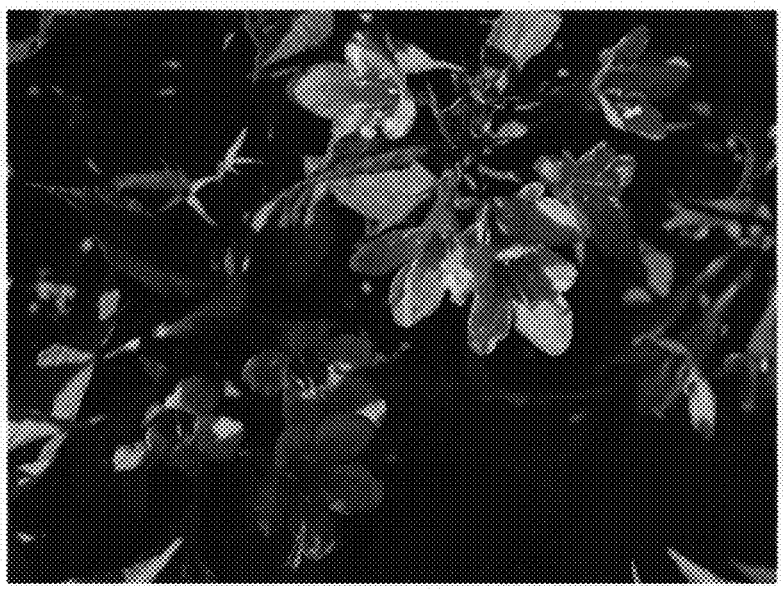

The photograph in FIG. 2 provides a close-up view of the flowers of 'TVP2'.

Figure 3:
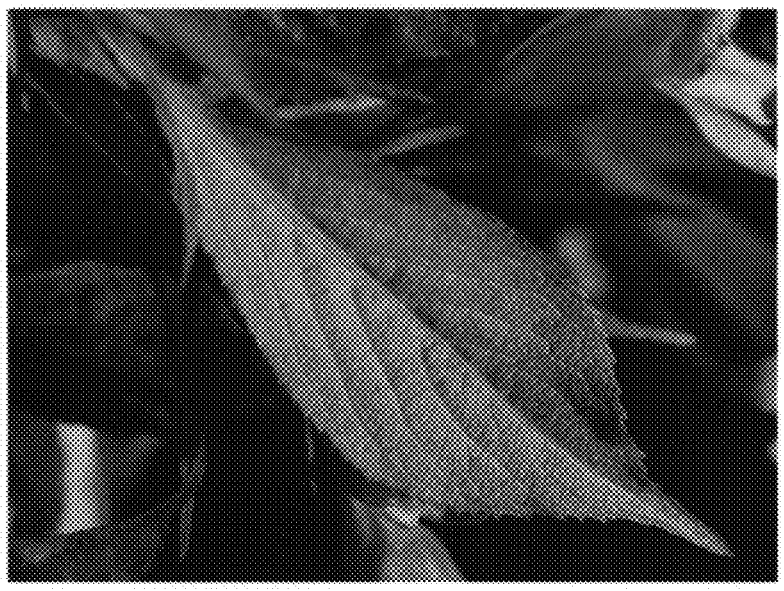

The photograph in FIG. 3 provides a close-up view of the foliage of 'TVP2'.

The colors in the photograph may differ slightly from the color values cited in the detailed botanical description, which accurately describe the colors of the new *Weigela.*

DETAILED BOTANICAL DESCRIPTION

The following is a detailed description of 14 month-old plants of the new cultivar as grown outdoors in a field in Hazerswoude-Dorp, The Netherlands. Phenotypic differences may be observed with variations in environmental, climatic, and cultural conditions. The color determination is in accordance with The 2015 R.H.S. Colour Chart of The Royal Horticultural Society, London, England, except where general color terms of ordinary dictionary significance are used.

General description:

*Blooming period.*—Remontant; blooms from late spring (May) and late summer to early fall (August to September) in The Netherlands.

*Plant type.*—Deciduous flowering shrub.

*Plant habit.*—Very compact, broadly upright and spreading, freely branched.

*Plant size.*—Reaches about 40 cm in height and 49 cm in width as a 14 month-old plant and 70 cm in height and 100 cm in width as a mature plant in the landscape.

*Cold hardiness.*—At least in U.S.D.A. Zone 5.

*Diseases and pests.*—No susceptibility to resistance to diseases or pests has been observed.

*Root description.*—Fibrous, moderately dense.

*Propagation.*—Softwood stem cuttings.

*Root initiation.*—An average of 6 weeks.

*Root development.*—An average of 3 months to produce a young rooted plant.

*Growth rate.*—Moderate.

Branch description:

*Branch shape.*—Rounded to slightly quadrangular.

*Branch color.*—New growth; 146C, mature wood; between 197D and 199D, bark; 199B.

*Branch size.*—An average of 14.8 cm in length and 2 mm in diameter.

*Branch surface.*—New growth; slightly glossy, sparsely covered with short hairs an average of 0.5 mm in length and 157D in color.

*Branch aspect.*—Upright to outward at an average angle of 32.5°.

*Branch strength.*—Moderately strong.

*Branching.*—An average of 11 main basal branches and 200 lateral branches.

*Internode length.*—Average of 3.2 cm.

Foliage description:

*Leaf shape.*—Elliptic to oblanceolate.

*Leaf division.*—Simple.

*Leaf base.*—Attenuate.

*Leaf apex.*—Apiculate.

*Leaf fragrance.*—None.

*Leaf aspect.*—Slightly carinate.

*Leaf venation.*—Pinnate, color upper surface N144A, color lower surface a color between 147B and 148B.

*Leaf margins.*—Serrate.

*Leaf arrangement.*—Opposite.

*Leaf attachment.*—Petiolate.

*Leaf surface.*—Both surfaces moderately non-rugose, smooth and glabrous, upper surface; main veins sparsely covered with soft pubescence an average of 0.2 mm in length and 157D in color, lower surface; main vein moderately covered with very short hairs average of 0.5 mm in length and 157D in color.

*Leaf size.*—An average of 5.8 cm in length and 1.9 cm in width.

*Leaf quantity.*—An average of 10 per lateral branch.

*Leaf color.*—Newly expanded leaves; upper and lower surface 144B, margins 166B, mature leaves; upper surface 147B, lower surface between 147B and 148B.

*Petioles.*—Average of 6 mm in length, 2 mm in width, upper surface color N144A lower surface color 151C, both surfaces are smooth, margins covered with soft pubescence 0.5 mm in length and 157D in color, strong.

*Stipules.*—None.

Inflorescence description:

*Inflorescence type.*—Solitary, in pairs, or in small clusters at terminus and leaf axils.

*Inflorescence size.*—7.2 cm in height, 5 cm in diameter.

*Flower buds.*—Oblanceolate in shape, an average of 2.6 cm in depth and 6 mm in diameter, 185B in color, matte surface.

*Flower fragrance.*—None.

*Lastingness of flowers.*—About 12 days, self-cleaning.

*Flower aspect.*—Outward to slightly upright.

*Flower quantity.*—An average of 8 per inflorescence, 500 buds and flowers per plant.

*Flower type.*—Tubular.

*Flower size.*—Average of 2.7 cm in height, 2.7 cm in diameter, 3.1 cm in depth, throat; 8 mm in diameter, tube; 2.2 cm in length, 7 mm in diameter.

*Peduncles.*—None, flowers attach directly to lateral stems.

*Calyx.*—Rotate in shape, an average of 1.1 cm in depth and 5 mm in width.

*Sepals.*—5, rotate, linear in shape, narrowly acute apex, cuneate base, entire margin, an average of 1 cm in length and 1 mm in width, lower 35% fused, both surfaces slightly glossy, color; when opening upper surface 145B and tinged N199C with tip N199B, when opening lower surface 145B and margined N199C, fully open upper surface 145C to 145D and tinged 177B, fully open lower surface 145C to 145D and margined 177C.

*Petals.*—5, lower 70% fused into tube, spathulate in shape, margin entire on free portion, apex obtuse, an average of 2.8 cm in length, 7 mm in width, upper and lower surface glabrous and slightly velvety, color; when opening upper surface 185B to 185C, when opening lower surface between 185A and 186A, when fully open upper surface a color between 53D and 186A, when fully open lower surface a color between 53C and 185B.

Reproductive organs:

*Gynoecium.*—Pistil; 1, average of 3.2 cm in length, style; average of 3.1 cm in length, and 155D in color, stigma; club-shaped, 1 mm in length and 2 mm in diameter, 155D in color, ovary; 144B and tinged 165B in color.

*Androcoecium.*—Stamens; 5, filaments; NN155D, fading towards the base to 187D in color and an average of 1.3 cm in length, anthers; 161D in color, an average of 3 mm in length, 0.5 mm in width, narrowly oblong in shape, pollen; moderate in quantity and 158D in color.

*Fruit and seed.*—No fruit or seed production has been observed.

It is claimed:

1. A new and distinct cultivar of *Weigela* plant named 'TVP2' as herein illustrated and described.

* * * * *